(12) United States Patent
Fursa (10) Patent No.: US 10,660,369 B2
(45) Date of Patent: May 26, 2020

(54) FLUID PERMEABLE HEATER ASSEMBLY AND CARTRIDGE FOR AN AEROSOL-GENERATING SYSTEM

(71) Applicant: Altria Client Services LLC, Richmond, VA (US)

(72) Inventor: Oleg Fursa, Lignieres (CH)

(73) Assignee: Altria Client Services LLC, Richmond, VA (US)

( * ) Notice: Subject to any disclaimer, the term of this patent is extended or adjusted under 35 U.S.C. 154(b) by 56 days.

(21) Appl. No.: 15/639,155

(22) Filed: Jun. 30, 2017

(65) Prior Publication Data

US 2018/0014575 A1   Jan. 18, 2018

Related U.S. Application Data

(63) Continuation of application No. PCT/EP2017/064965, filed on Jun. 19, 2017.

(30) Foreign Application Priority Data

Jul. 14, 2016 (EP) .................................... 16179478

(51) Int. Cl.
*A24F 47/00* (2020.01)
*A61M 11/04* (2006.01)
*A61M 15/06* (2006.01)

(52) U.S. Cl.
CPC ......... *A24F 47/008* (2013.01); *A61M 11/042* (2014.02); *A61M 15/06* (2013.01); *A61M 2205/3653* (2013.01); *A61M 2205/8206* (2013.01)

(58) Field of Classification Search
None
See application file for complete search history.

(56) References Cited

FOREIGN PATENT DOCUMENTS

| WO | WO-2015/117702 A1 | 8/2015 |
| WO | WO-2015/117704 A1 | 8/2015 |
| WO | WO-2015177045 A1 | 11/2015 |
| WO | WO-2016/005533 A1 | 1/2016 |
| WO | WO-201600553 A1 | 1/2016 |
| WO | WO-2016005602 A1 | 1/2016 |
| WO | WO-2016023809 A1 | 2/2016 |

OTHER PUBLICATIONS

Extended European Search Report application No. 16179478.9 dated Feb. 8, 2017.
U.S. Appl. No. 15/393,605, filed Dec. 29, 2016.
U.S. Appl. No. 15/607,928, filed May 30, 2017.
International Search Report and Written Opinion for Application No. PCT/EP2017/064965 dated Sep. 19, 2017.
International Preliminary Report on Patentability and Written Opinion for corresponding International Application No. PCT/EP2017/064965 dated Jan. 15, 2019.

*Primary Examiner* — Michael J Felton
*Assistant Examiner* — Katherine A Will
(74) *Attorney, Agent, or Firm* — Harness, Dickey & Pierce, P.L.C.

(57) ABSTRACT

A fluid permeable heater assembly for an aerosol-generating system includes a base including an opening through the base and an electrically conductive filament arrangement over the opening. The base includes a solid aerosol-forming substrate on the base. A cartridge includes a cartridge body including a reservoir within the cartridge body. A heater assembly is arranged at one end of the cartridge body.

10 Claims, 2 Drawing Sheets

FLUID PERMEABLE HEATER ASSEMBLY AND CARTRIDGE FOR AN AEROSOL-GENERATING SYSTEM

CROSS-REFERENCE TO RELATED APPLICATIONS

This application is a continuation of, and claims priority to, international application no. PCT/EP2017/064965, filed on Jun. 19, 2017, and further claims priority under 35 U.S.C. § 119 to European Patent Application No. 16179478.9, filed Jul. 14, 2016, the entire contents of each of which are incorporated herein by reference.

BACKGROUND

Field

Example embodiments relate to a heater assembly and a cartridge for an aerosol-generating system.

Description of Related Art

Smoking systems may heat a tobacco containing substrate rather than combusting the tobacco containing substrate. A nicotine containing product may be vaporized, for example using a cartomizer, wherein an aerosol-forming liquid containing cartridge is directly combined with a heater that heats and evaporates the liquid. Cigarettes may be heated and combined with the cartomizers.

SUMMARY

At least one example embodiment relates to a fluid permeable heater assembly.

In at least one example embodiment, a fluid permeable heater assembly for an aerosol-generating system includes an electrically conductive filament arrangement and a base defining an opening through the base. The base includes a solid aerosol-forming substrate on the base, and a thermally conductive material configured to conduct heat from the electrically conductive filament arrangement to the solid aerosol-forming substrate. The electrically conductive filament arrangement is over the opening of the base.

In at least one example embodiment, the solid aerosol-forming substrate is in the form of one of an aerosol-forming sheet applied to the base and a base coating. In at least one example embodiment, the solid aerosol-forming substrate is on a top side of the base. In at least one example embodiment, the solid aerosol-forming substrate is in contact with portions of the electrically conductive filament arrangement. In at least one example embodiment, the solid aerosol-forming substrate is a solid tobacco containing aerosol-forming substrate.

In at least one example embodiment, the heater assembly is a flat fluid permeably heater assembly, and the filament arrangement is a flat filament arrangement.

At least one example embodiment relates to a cartridge for an aerosol-generating device.

In at least one example embodiment, a cartridge for an aerosol-generating device includes a reservoir in the cartridge body. The reservoir is configured to store an aerosol-forming liquid. The cartridge also includes a heater assembly at one end of the cartridge body. The heater assembly is configured to receive the aerosol-forming liquid from the reservoir. The heater assembly includes an electrically conductive filament arrangement and a base defining an opening through the base. The base includes a solid aerosol-forming substrate on the base, and a thermally conductive material configured to conduct heat from the electrically conductive filament arrangement to the solid aerosol-forming substrate. The electrically conductive filament arrangement is over the opening of the base. The cartridge also includes electrical contacts configured to engage corresponding electrical contacts in an aerosol-generating device. The heater assembly is configured to heat the aerosol-forming liquid received from the reservoir.

In at least one example embodiment, the cartridge body defines an outlet opening. The outlet opening is aligned with the opening in the base of the heater assembly. The heater assembly and the cartridge body are arranged such that the solid aerosol-forming substrate is on a top side of the heater assembly away from the cartridge body.

In at least one example embodiment, the opening of the base of the heater assembly is in a central portion of the cartridge and the solid aerosol-forming substrate is arranged circumferentially around the opening. The reservoir contains a nicotine-containing aerosol-forming liquid and the solid aerosol-forming substrate contains tobacco.

At least one example embodiment relates to an electrically operated aerosol-generating system.

In at least one example embodiment, an electrically operated aerosol-generating system comprises a storage portion including, a housing configured to hold a liquid aerosol-forming substrate and a fluid permeable heater assembly. The housing has an open end. The fluid permeable heater assembly includes an electrically conductive filament arrangement and a base defining an opening through the base. The base includes a solid aerosol-forming substrate on the base, and a thermally conductive material configured to conduct heat from the electrically conductive filament arrangement to the solid aerosol-forming substrate. The electrically conductive filament arrangement is over the opening of the base. The fluid permeable heater assembly is arranged next to the housing such that the filament arrangement of the fluid permeable heater assembly is over the open end of the housing. The electrically operated aerosol-generating system also includes a power source and a connector configured to electrically connect the filament arrangement of the fluid permeable heater assembly to the power source.

In at least one example embodiment, the electrically operated aerosol-generating system includes a cartridge. The cartridge includes a reservoir in the housing. The reservoir is configured to store the liquid aerosol-forming substrate. The cartridge also includes a heater assembly at one end of a cartridge body. The heater assembly is configured to receive the aerosol-forming liquid from the reservoir. The heater assembly includes an electrically conductive filament arrangement and a base defining an opening through the base. The base includes a solid aerosol-forming substrate on the base, and a thermally conductive material configured to conduct heat from the electrically conductive filament arrangement to the solid aerosol-forming substrate. The electrically conductive filament arrangement is over the opening of the base. The cartridge also includes electrical contacts configured to engage corresponding electrical contacts in an aerosol-generating device. The heater assembly is configured to heat the aerosol-forming liquid received from the reservoir. The housing is in the cartridge body.

In at least one example embodiment, the aerosol-generating system further comprises an aerosol-generating device 
including a main body defining a cavity. The cavity is configured to receive the cartridge.

BRIEF DESCRIPTION OF THE DRAWINGS

Example embodiments are further described and illustrated by the following drawings.

DETAILED DESCRIPTION

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms “a”, “an” and “the” are intended to include the plural forms as well, unless the context clearly indicates otherwise. It will be further understood that the terms “comprises,” “comprising,” “includes,” and/or “including,” when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being “on”, “connected to” or “coupled to” another element or layer, it can be directly on, connected or coupled to the other element or layer or intervening elements or layers may be present. In contrast, when an element is referred to as being “directly on”, “directly connected to” or “directly coupled to” another element or layer, there are no intervening elements or layers present. As used herein, the term “and/or” includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as “beneath”, “below”, “lower”, “above”, “upper”, and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as “below” or “beneath” other elements or features would then be oriented “above” the other elements or features. Thus, the example term “below” can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as “processing” or “computing” or “calculating” or “determining” or “displaying” or the like, refer to the action and processes of a computer system, or similar electronic computing device, that manipulates and transforms data represented as physical, electronic quantities within the computer system’s registers and memories into other data similarly represented as physical quantities within the computer system memories or registers or other such information storage, transmission or display devices.

At least one example embodiment relates to a fluid permeable heater assembly for an aerosol-generating system. The fluid permeable heater assembly comprises a base. The base defines an opening through the base. The fluid permeable heater assembly also includes an electrically conductive filament arrangement arranged over the opening. The base comprises solid aerosol-forming substrate on the base. The base also comprises a thermally conductive material arranged to conduct heat from the electrically conductive filament arrangement to the solid aerosol-forming substrate.

Fluid permeable heaters may be used in combination with a liquid reservoir. Fluid permeable heaters are configured to heat and evaporate an aerosol-forming liquid, for example a nicotine containing liquid, by heating the filament arrangement in the heater assembly.

By providing a heater assembly with solid aerosol-forming substrate, substances from the heated solid aerosol-forming substrate may be added to aerosol formed by evaporated liquid heated by the filament arrangement of the heater assembly. In at least one example embodiment, tobacco flavours contained in the solid substrate containing tobacco or tobacco material may be added to the aerosol.

In at least one example embodiment, residual heat from the filament arrangement may be used for heating the solid aerosol-forming substrate.

Thus, such heater assemblies may provide high energy efficiency in that residual heat not available for evaporating liquid by the filament arrangement may be used for vaporizing substances from the solid substrate on the heater, such as tobacco flavour.

The residual heat from a heater assembly may have significant heat losses from a heater filament to the surrounding heater area. For example heaters using several strips of mesh arranged in parallel may cause surrounding surfaces to be heated as well.

With the heater assembly, it may be possible to vaporize aerosol-forming liquid and generate additional evaporated substances from the solid substrate using a same amount of energy required for vaporizing the liquid. Also, less efficient and possibly less costly heaters may be used for vaporizing liquid without waste of heat generated by the heater.

As used herein, the term 'aerosol-forming substrate' relates to a substrate configured to release volatile compounds that can form an aerosol. Such volatile compounds may be released by heating the aerosol-forming substrate.

The solid aerosol-forming substrate may be in the form of an aerosol-forming sheet applied to the base of the heater assembly.

The solid aerosol-forming substrate may be in the form of a base coating.

The solid aerosol-forming substrate may be applied to the base of the heater assembly prior, during or after assembly of the heater assembly. In at least one example embodiment, the solid aerosol-forming substrate is applied to the heater assembly after assembly of the heater assembly. In at least one example embodiment, the solid aerosol-forming substrate is on the heater assembly excluding that portion of the filament arrangement arranged in the opening of the base.

In at least one example embodiment, a solid aerosol-forming substrate is arranged on a top side of the base of the heater assembly. The solid aerosol-forming substrate may be arranged on a top side of the base excluding the opening. The solid aerosol-forming substrate may be arranged on a top side of the base only. The solid aerosol-forming substrate may be arranged on an entire top side of the base.

In at least one example embodiment, the solid aerosol-forming substrate is at least provided in contact portions of the filament arrangement. Contact portions of the filament arrangement may comprise opposite ends of the filament arrangement. Contact portions may extend over the base of the heater assembly on opposite sides of the opening in the base. The solid aerosol-forming substrate may be arranged in contact portions of the filament arrangement only.

A coating of the base with aerosol-forming substrate provides a very close and direct physical contact between the substrate coating and the base or with the coating and contact regions of the base. Thus, heat transfer from the base to the coating is increase (e.g., optimized). The close contact leads to a fast heating up of the coating.

The provision of the base with a sheet of aerosol-forming substrate, for example a cast leaf, enables the manufacture of the sheet independently from the heater assembly. A piece of sheet to be applied to the heater may be cut to the exact size required and may be positioned on the heater in those regions intended therefor.

In at least one example embodiment, the base material comprises a single aerosol-forming substrate coating or a single sheet of aerosol-forming substrate.

The effect of the solid aerosol-forming substrate may be dependent on the heating but also on the thickness and consistency of the solid aerosol-forming substrate, for example, on a coating process or application process.

A thickness of an aerosol-forming substrate coating may range from about 80 micrometers to about 1 millimeter, from about 100 micrometers to about 600 micrometers, or from about 100 micrometers to about 400 micrometers.

The sheet of aerosol-forming substrate may have a thickness ranging from about 0.1 millimeter to about 2 millimeters, from about 0.3 millimeter to about 1.5 millimeters, or about 0.8 millimeter.

Whenever a value is mentioned throughout this application, this is to be understood such that the value is explicitly disclosed. However, a value is also to be understood as not having to be exactly the particular value due to technical considerations.

A coating of the heater assembly may be performed by coating processes suitable for coating a base material with aerosol-forming substrate slurry.

In at least one example embodiment, the aerosol-forming substrate coating is performed by one of deposition, dip-coating, spraying, painting or casting of aerosol-forming substrate slurry onto an uncoated base.

These coating methods are industrial processes that allow for mass production of coated objects. These coating processes also enable product consistency in production and repeatability in performance of the heater assembly.

The solid aerosol-forming substrate may comprise a tobacco-containing material containing volatile tobacco flavour compounds, which are released from the substrate upon heating. In at least one example embodiment, the aerosol-forming substrate may comprise a non-tobacco material. The aerosol-forming substrate may further comprise an aerosol former. Examples of suitable aerosol formers are glycerine and propylene glycol.

The aerosol-forming substrate may contain one or more of: herb leaf, tobacco leaf, fragments of tobacco ribs, reconstituted tobacco, homogenised tobacco, extruded tobacco, and expanded tobacco.

The solid aerosol-forming substrate may also contain microcapsules that, for example, include the additional tobacco or non-tobacco volatile flavour compounds. The microcapsules may melt during heating of the solid aerosol-forming substrate.

The solid aerosol-forming substrate may comprise one or more sheets of homogenised tobacco material. In at least one example embodiment, the solid aerosol-forming substrate is a sheet of homogenised tobacco material.

Tobacco containing slurry and a tobacco sheet as well as a coating made from the tobacco containing slurry comprises tobacco particles, fiber particles, aerosol former, binder and for example also flavours.

In at least one example embodiment, the aerosol-forming tobacco substrate is a tobacco sheet comprising tobacco material, fibers, binder and aerosol former. In at least one example embodiment, the tobacco sheet is a cast leaf. Cast leaf is a form of reconstituted tobacco that is formed from a slurry including tobacco particles, fiber particles, aerosol former, binder and for example also flavours.

In at least one example embodiment, a coating is a form of reconstituted tobacco that is formed from the tobacco containing slurry.

Tobacco particles may be of the form of a tobacco dust having particles ranging in size from about 30 micrometers to about 250 micrometers, depending on the coating thickness or an a sheet thickness and casting gap, where the casting gap typically defines the thickness of the sheet.

Fiber particles may include tobacco stem materials, stalks or other tobacco plant material, and other cellulose-based fibers such as wood fibers having a low lignin content.

Aerosol formers included in the slurry for forming the cast leaf and the coating may be chosen based on one or more characteristics. An aerosol former may be chosen based on its ability, for example, to remain stable at or around room temperature but able to volatize at a higher temperature ranging from about 40 degree Celsius to about 250 degree Celsius. The aerosol former may also have humectant type properties that help maintain a desired (or, alternatively predetermined) level of moisture in an aerosol-forming substrate.

One or more aerosol formers may be combined. For example, triacetin may be combined with glycerol and water.

In at least one example embodiment, the tobacco containing slurry to produce a cast leaf or a slurry for an aerosol-forming substrate coating comprises homogenized tobacco material and comprises glycerol or propylene glycol as aerosol former. In at least one example embodiment, the aerosol-forming substrate is made of a tobacco containing slurry as described above.

In at least one example embodiment, a solid aerosol-forming substrate is porous to allow volatilized substances to leave the substrate. A solid substrate with small thickness may, for example, be chosen to have less porosity than a solid substrate with larger thickness.

The base of the heater assembly may comprise any suitable material, and is a material that is able to tolerate high temperatures (in excess of about 300 degrees Celsius) and rapid temperature changes.

In at least one example embodiment, the material of the base is non-brittle. The base material may have capillary action for liquid to be vaporized.

The base comprises or is made of thermally conductive material. Thermally conductive material is arranged to conduct heat from the electrically conductive filament arrangement to the solid aerosol-forming substrate. The base may be entirely thermally conductive or only in regions where solid substrate is present. For example, a periphery around the opening in the base may be provided with a thermally conductive layer.

With thermally conductive material in or on the base distribution of heat from the filament arrangement may be supported. In at least one example embodiment, more homogeneous heat distribution and heat distribution over, for example an entire top side of a base may be supported.

Thermal conductivity is the capacity of a material to conduct heat. Heat transfer occurs at a lower rate across materials of low thermal conductivity than across materials of high thermal conductivity. The thermal conductivity of a material may depend on temperature.

Thermally conductive materials may be included as base materials or thermally conductive layers provided on the base. The term 'thermally conductive material' refers to materials having thermal conductivities of more than about 10 Watt per (meter×Kelvin), more than about 100 Watt per (meter×Kelvin), or from about 10 Watt per (meter×Kelvin) to about 500 Watt per (meter×Kelvin).

Suitable thermally conductive materials include, but are not limited to, metals such as, for example, aluminium, chromium, copper, gold, iron, nickel and silver, alloys, such as brass, steel and stainless steel and combinations thereof. Thermally conductive material is favourable in view of heat transfer and in view of heat distribution. By arranging thermally conductive material on the base as support material below the solid aerosol-forming substrate and in close contact with the heating region of the heater assembly, heat from the heated filament arrangement may be used for heating the solid aerosol-forming substrate. Thermally conductive material may also support a homogenous heat temperature distribution in the solid aerosol-forming substrate.

Thermally conductive material may, for example, also be ceramic material. If as thermally conductive material also electrically conductive material is used, such as metals or alloys, the filament arrangement should be electrically isolated from an electrically and thermally conductive layer.

In at least one example embodiment, the solid aerosol-forming substrate is a solid tobacco containing aerosol-forming substrate that enables and/or enhances a tobacco flavor content of an aerosol generated in an aerosol-forming device or system the heater assembly.

The heater assembly may, for example, be a mesh heater.

In at least one example embodiment, the heater assembly is a flat fluid permeable heater assembly and the filament arrangement is a flat filament arrangement.

The term 'flat' filament arrangement or 'flat' heater assembly is used throughout the specification to refer to a filament arrangement or a flat heater assembly that is in the form of a substantially two dimensional topological manifold. Thus, the flat filament arrangement and flat heater assembly extend in two dimensions along a surface substantially more than in a third dimension. In at least one example embodiment, the dimensions of the flat filament arrangement in the two dimensions within the surface is at least 5 times larger than in the third dimension, normal to the surface. An example of a flat filament arrangement and a flat heater assembly is a structure between two substantially parallel imaginary surfaces, wherein the distance between these two imaginary surfaces is substantially smaller than the extension within the surfaces. In at least one example embodiment, the flat filament arrangement and the flat heater assembly is planar. In at least one example embodiment, the flat filament arrangement and the flat heater assembly are curved along one or more dimensions, for example forming a dome shape or bridge shape.

A flat filament arrangement may be used in a flat heating element, which can be easily handled during manufacture and provides for a robust construction.

The term 'filament' is used throughout the specification to refer to an electrical path arranged between two electrical contacts. A filament may arbitrarily branch off and diverge into several paths or filaments, respectively, or may converge from several electrical paths into one path. A filament may have a round, square, flat or any other form of cross-section. A filament may be arranged in a straight or curved manner.

The term 'filament arrangement' is used throughout the specification to refer to an arrangement of one or a plurality of filaments. The filament arrangement may be an array of filaments, for example arranged parallel to each other. In at least one example embodiment, the filaments may form a mesh. The mesh may be woven or non-woven. In at least one example embodiment, the filament arrangement has a thickness ranging from about 0.5 micrometer to about 500 micrometers. The filament arrangement may, for example, be in the form of an array of parallel or crosswise electrically conductive filaments. The filament may be integrally formed with electrical contacts, for example formed from an electrically conductive foil, for example, stainless steel foil, that is etched to define the filaments or openings in the center portion as well as in the side portions or in the center surface and side surfaces, respectively.

In at least one example embodiment, the filament arrangement is in the form of a mesh.

The area of a mesh, array, or fabric of electrically conductive filaments may be small, for example less than or equal to about 25 mm$^2$, so as to allow the mesh, array, or fabric to be incorporated into a handheld system. The mesh, array, or fabric of electrically conductive filaments may, for example, be rectangular and have dimensions of about 5 mm by about 2 mm. In at least one example embodiment, the mesh or array of electrically conductive filaments covers an area ranging from about 10% of the area of the heater assembly to about 50% of the area of the heater assembly. In at least one example embodiment, the mesh or array of electrically conductive filaments covers an area ranging from about 15% of the area of the heater assembly to about 25% of the area of the heater assembly. Sizing of the mesh, array, or fabric of electrically conductive filaments to about 10% to about 50% of the area, or less or equal than 25 mm2, reduces the amount of total power required to heat the mesh, array, or fabric of electrically conductive filaments while still ensuring sufficient contact of the mesh, array or fabric of electrically conductive filaments to the liquid, provided to the filament arrangement by one or more capillary materials, to be volatilized.

The filament arrangement may be held on the base by directly moulding the filament arrangement and base material together. However, the filament arrangement may also be held on the base by fastener.

A fastener may be electrically conductive and may serve as electrical contact for providing heating current through the filament arrangement.

A fastener may be a chemical or mechanical fastener. The filament arrangement may, for example be attached to the substrate by bonding or gluing.

In at least one example embodiment, a fastener is a mechanical fastener such as clamps, screws, or form-locking fastener.

The fastener may be one or a combination of the aforementioned fastener.

At least one example embodiment relates to a cartridge for use in an aerosol-generating device or system. The cartridge comprises a cartridge body including a reservoir within the cartridge body. The reservoir is configured to store an aerosol-forming liquid. The cartridge also includes a heater assembly according to any of the example embodiments described herein. The heater assembly is arranged at one end of the cartridge body, and is configured to receive the aerosol-forming liquid from the reservoir. The solid aerosol-forming substrate is arranged on the base of the heater assembly. The cartridge further comprises electrical contacts, which are configured to engage corresponding electrical contacts in an aerosol-generating device. The electrical contacts may be electrically connected to the filament arrangement of the heater assembly. In the cartridge, the heater assembly is configured to heat aerosol-forming liquid received from the reservoir. Thereby residual heat from heating the filament arrangement of the heater assembly heats the solid aerosol-forming substrate of the heater assembly. The cartridge body is open and the one end for aerosol-forming liquid to leave the cartridge body. The cartridge body may comprise an outlet opening, aligned with the opening in the base of the heater assembly. The outlet opening may, for example, be an outlet opening of a flow channel through the cartridge body. The outlet opening may also be an outlet opening in the cartridge body for a wick material or high retention material contained in the cartridge, where liquid contained in the cartridge may come into contact with the filament arrangement of the heater assembly.

The outlet opening of the cartridge body and the opening in the base may have a same size.

The opening of the base of the heater assembly may be arranged in a central portion of the cartridge, that is, in a central portion of the one end of the cartridge body. In at least one example embodiment, the solid aerosol-forming substrate is then arranged circumferentially around the opening in the base of the heater assembly.

In the cartridge, the heater assembly and the cartridge body may be arranged such that the solid aerosol-forming substrate is on a top side of the heater assembly directing away from the cartridge body. In at least one example embodiment, the solid substrate is on a top side of a base of a flat heater assembly, wherein the flat heater assembly is substantially perpendicular to the one end of the cartridge body, for example, perpendicular to the one end of a longitudinal cartridge body.

The cartridge body and the heater assembly may both have a circular shape. The cartridge body and the heater assembly may have a same diameter or substantially a same diameter.

A reliable contact between the fluid permeable heater assembly and a transport medium, for example a capillary transport medium such as a wick made from fibres or a porous ceramic material, may improve a constant wetting of the filament arrangement of the fluid permeable heater assembly, and may reduce the risk of overheating of the electrically conductive filament arrangement and inadvertent thermal decomposition of the liquid.

The reservoir or liquid storage portion in the cartridge body may contain a capillary material. A capillary material is a material that actively conveys liquid from one end of the material to another. The capillary material is oriented in the cartridge body to convey liquid to the heater assembly.

The capillary material may have a fibrous or spongy structure. The capillary material comprises a bundle of capillaries. For example, the capillary material may comprise a plurality of fibres or threads or other fine bore tubes. The fibres or threads may be generally aligned to convey liquid to the heater assembly. In at least one example embodiment, the capillary material may comprise sponge-like or foam-like material. The structure of the capillary material forms a plurality of small bores or tubes, through which the liquid can be transported by capillary action. The capillary material may comprise any suitable material or combination of materials. Examples of suitable materials are a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

The capillary material may be in contact with the electrically conductive filaments of the filament arrangement. The capillary material may extend into interstices between the filaments. The heater assembly may draw liquid aerosol-forming substrate into the interstices by capillary action. The capillary material may be in contact with the electrically conductive filaments over substantially the entire extent of the opening in the base. In one embodiment the capillary material in contact with the electrically conductive filament arrangement may be a filamentary wick. In at least one example embodiment, the filamentary wick has a first section and a second section, wherein the first section is arranged substantially perpendicular to the electrically conductive filament arrangement, reaching into the reservoir of the cartridge. In at least one example embodiment, the second section of the filamentary wick is arranged substantially in parallel to the electrically conductive filament arrangement. In at least one example embodiment, the filaments of the filamentary wick are continuous from the first section of the filamentary wick to the second section of the filamentary wick. This allows a quick transport of the liquid towards the electrically conductive filament arrangement through the first section of the filamentary wick and, at the same time, a quick distribution across the electrically conductive filament arrangement through the second section of the filamentary wick, which may allow a continuous wetting of the entire electrically conductive filament arrangement. A continuous wetting may reduce and/or avoid overheating and reduce and/or substantially prevent the inadvertent decomposition of the liquid due to the overheating.

The heater assembly and the capillary material may be sized to have about the same area. As used here, about means that the heater assembly may be between 0-15% larger than the capillary material. The shape of the heater assembly may also be similar to the shape of the capillary material such that the assembly and the material substantially overlap. When the assembly and the material are substantially similar in size and shape, manufacturing can be simplified and the robustness of the manufacturing process improved. The capillary material may include two or more capillary materials including one or more layers of the capillary material directly in contact with the mesh, array or fabric of electrically conductive filaments of the heater assembly in order to promote aerosol generation.

In at least one example embodiment, the reservoir of the cartridge comprises aerosol-forming liquid, for example nicotine containing liquid, and the solid aerosol-forming substrate contains tobacco.

According to at least one example embodiment, there is provided an electrically operated aerosol-generating system. The system comprises a storage portion comprising a housing for holding a liquid aerosol-forming substrate. The housing has an open end. The system further comprises a fluid permeable heater assembly as described herein. The heater assembly is arranged next to the housing such that the filament arrangement of the fluid permeable heater assembly is arranged over the open end of the housing. The system further comprises a power source and a connector of a power source. The power source is configured to electrically connect the filament arrangement of the fluid permeable heater assembly to the power source.

In at least one example embodiment, the aerosol-generating system is a system that is configured to provide aerosol without combusting tobacco.

In such a system, the housing holding the liquid aerosol-forming substrate may be positioned on a first side of the electrically conductive filaments and an airflow channel may be positioned on an opposite side of the electrically conductive filaments to the liquid storage portion. By this arrangement, an air flow past the electrically conductive filaments may entrain vapourised liquid aerosol-forming substrate from the substrate as well as vaporised substances from the solid aerosol-forming substrate on the heater assembly.

The housing of the storage portion may comprise two elements. The first element is a cap and the second element is a tank. The cap closes the tank. In at least one example embodiment, the cap comprises or is in close contact with the heater assembly. In at least one example embodiment, the tank comprises the liquid, and where present the capillary material. In at least one example embodiment, the cap material is made from a material with a high thermal decomposition temperature, such as for example polyetheretherketone (PEEK) or Kapton®. In at least one example embodiment, the cap has a size sufficient to distance the tank from the heater assembly by a distance of at least about 1.5 mm, or from about 1.5 min to about 2 mm in order to provide a sufficient temperature drop across the cap. In at least one example embodiment, the tank material can be made from a more cost efficient material with a lower thermal decomposition temperature, such as for example polyethylene or polypropylene.

The housing and the heater assembly may be separate parts fixedly or removably mounted in the system. The housing and the heater assembly may also be constructed as a unit, for example in the form of a cartridge.

The system may include a cartridge according to at least one example embodiment. The cartridge includes a cartridge body comprising the housing. The housing is configured to hold the liquid aerosol-forming substrate.

The system may comprise an aerosol-generating device and a cartridge that is removably coupled to the device. The reservoir or liquid storage portion and heater assembly are provided in the cartridge and the aerosol-generating device comprises the power supply.

The device may comprise a main body defining a cavity. The cavity is configured to receive the cartridge.

The aerosol-generating system may further comprise electric circuitry connected to the heater assembly and to an electrical power source. The electric circuitry may be configured to monitor the electrical resistance of the heater assembly or of one or more filaments of the heater assembly, and to control the supply of power to the heater assembly dependent on the electrical resistance of the heater assembly or the one or more filaments.

The electric circuitry may comprise a microprocessor, which may be a programmable microprocessor. The electric circuitry may comprise further electronic components. The electric circuitry may be configured to regulate a supply of power to the heater assembly. Power may be supplied to the heater assembly substantially continuously following activation of the system or may be supplied intermittently, such as on a puff-by-puff basis. The power may be supplied to the heater assembly in the form of pulses of electrical current.

The power supply of the system is a battery, for example within the main body of an aerosol-generating device. The power supply may require recharging and may have a capacity that allows for the storage of enough energy for one or more smoking experiences. In at least one example embodiment, the power supply may have sufficient capacity to allow for the continuous generation of aerosol for a period of around six minutes or for a period that is a multiple of six minutes. In at least one example embodiment, the power supply may have sufficient capacity to allow for a desired (or, alternatively predetermined) number of puffs or discrete activations of the heater assembly.

In at least one example embodiment, the aerosol-generating device may include features as set forth in U.S. Ser. No. 15/393,605 filed Dec. 29, 2016 and/or U.S. Ser. No. 15/607,928 filed May 30, 2017, the entire contents of each of which are incorporated herein by reference thereto.

Figure 1:
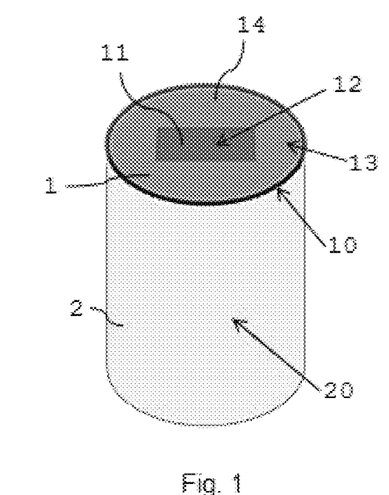
FIGS. 1 and 2 are schematic illustrations of a cartridge according to at least one example embodiment.
Figure 2:
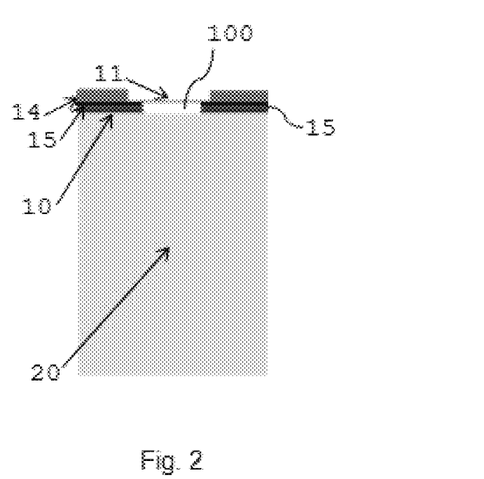

FIG. 1 is a schematic perspective topside view of a cartridge formed by a cartridge 2 and a heater assembly 1. FIG. 2 shows the cartridge in a schematic longitudinal cross-sectional view.

The heater assembly 1 extends in a lateral plane and is flush with the housing 20 of the cartridge 2 along the circumference of the heater assembly 1 and the housing 20. The housing 20 has a cylindrical shape and may comprise high retention material, capillary material, or may be an empty tank configured to receive and hold liquid aerosol-forming substrate.

The heater assembly 1 is a substantially flat heater having the form of a disk.

The heater assembly 1 comprises a disk-shaped base 10 comprising a central opening 100 and a filament arrangement 11 arranged over the opening 100 and attached to the base 10. The filament arrangement 11, for example a mesh arrangement, is attached to the base 10 by integral moulding, by mechanical fastener, or by chemical fastener. For example, the filament arrangement 11 may be attached to the base 10 by clamps, screws, bonding or adhesive.

On the base 10, except for the heating region 12 or except for the opening 100 provided in the base 10, respectively, a solid aerosol-forming substrate layer 14 is provided. The layer 14 may be a tobacco material containing layer covering the base 10 and portions of the filament arrangement 14 extending over the base, for example in contact portions 13 of the filament arrangement.

The base 10 may be provided with the aerosol-forming substrate layer 14 by coating, dipping, spraying or other suitable application methods. The base 10 may also be provided with a premanufactured layer 14, which is applied to the base 10 after manufacturing of the layer. If an aerosol-forming substrate coating is provided, a heating region 12 and filament arrangement 11 in the heating region 12 is covered or otherwise protected such that the filament arrangement in the heating region is not provided with the solid an aerosol-forming substrate of the aerosol-forming substrate layer 14. The thickness of the layer 14 is about 1 millimeter.

In at least one example embodiment, the base 10 is electrically isolating. For better heat distribution of the heat generated by the filament arrangement 11 in the contact regions 13, over the entire surface of the base or over the entire aerosol-forming substrate layer 14, a thermally conductive layer 15, such as a ceramic material or a metal, may be arranged on a top side of the base. The thermally conductive layer 15 substantially covers the same area of the base 10 as the aerosol-forming substrate layer 14.

In at least one example embodiment, as shown in FIG. 2, the thermally conductive layer 15 is arranged between the base 10 and the filament arrangement 11. However, contacts of the filament arrangement 11 and the thermally conductive layer 14 are electrically isolated.

The heater filaments of the filament arrangement of the heating region 12 are exposed through the opening 100 in the base 10 so that vapourised aerosol-forming substrate can escape into an air flow past the heater assembly.

The housing 20 is formed from a thermoplastic, such as polypropylene. The heater assembly 1 may be glued to the housing 20. However, there are several possible ways in which to assembly and fill the cartridge.

The cartridge housing may be formed by injection moulding. Capillary material present in the housing 10 may be formed by cutting suitable lengths of capillary material from a long rod of capillary fibres. The cartridge may be assembled by first inserting the capillary material into the housing 20. A desired (or, alternatively predetermined) volume of the liquid aerosol-forming substrate is then introduced into the housing 20, soaking the capillary material. The heater assembly 1 is then pushed onto the open end of the housing and fixed to the housing 20 by gluing, welding, heat sealing, ultrasonic welding, or other methods. The temperature of the housing is held below about 160° C. or lower during any sealing operation to reduce and/or substantially prevent unwanted volatising of the liquid aerosol-forming substrate in the housing 20 or of the solid aerosol-forming substrate of the layer 14 on the heater assembly 1 if present upon assembly of heater 1 and housing 20. The capillary material may be cut to a length such that it extends out of an open end of the housing 20 until it is compressed by the heater assembly 1. This promotes transport of liquid aerosol-forming substrate into the interstices of the heater element in use.

In at least one example embodiment, the housing is filled with the liquid aerosol-forming substrate and then assembled with the heater assembly 1. The heater assembly 1 and the housing 20 may be assembled before filling the housing with the liquid aerosol-forming substrate and subsequently to introducing the liquid aerosol-forming substrate into the housing 20. In at least one example embodiment, the heater assembly 1 may be fixed to the cartridge housing 20 using any of the methods described. The heater assembly 1 or housing 2 is then pierced using a hollow needle and the liquid aerosol-forming substrate injected into the housing, for example into the capillary material in the housing. Any opening made by the hollow needle is then sealed by heat sealing or by using a sealing tape.

In at least one example embodiment, the aerosol-forming substrate layer 14 is on the heater assembly 1 before heater assembly 1 and cartridge housing 20 are assembled. However, assembly of heater and housing may be performed and after complete assembly, the solid aerosol-forming layer 14 may be provided to the otherwise final cartridge. By this method pre-manufactured cartridges may be utilized. These cartridges may be provided with a solid aerosol-forming substrate layer 14 to improve a smoking experience and make use of residual heat of the heater assembly 1, in particular generated in contact portions.

Figure 3:
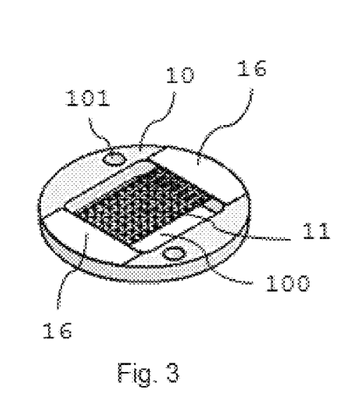
FIG. 3 is an illustration of a mesh heater according to at least one example embodiment.

FIG. 3 schematically shows an example of a set-up of a flat, fluid-permeable heater assembly with a mesh arrangement 11. In the assembled state of the heater as shown in FIG. 3, the heater assembly comprises an electrically insulating base 10, a heater element and filament arrangement in the form of a mesh arrangement 11 and two metal sheets 16. The metal sheets 16 may, for example, be sheets of tin, to alter electrical contact of connectors, for example contact pins, with the side portions of the mesh arrangement 11 where the mesh arrangement is contacted.

The base 10 has the form of a circular disc and comprises a centrally arranged opening 100. The base 10 comprises two bore holes 101 arranged diagonally opposite each other in the substrate. The bore holes 101 may serve for positioning and mounting the heater assembly for example on a cartridge housing or in an aerosol-generating device.

The mesh arrangement 11 comprises a heating region and possibly two PEEK overmoulded contact regions. The mesh arrangement is arranged over the square-formed centrally arranged opening 100 and over parts of the base 10. The heating region of the mesh arrangement comes to lie over the opening 100. The two contact regions, in particular those portions of the mesh overmoulded with PEEK and tin-plated (covered with the metal sheets 6) come to lie on the base 10.

The width of the mesh in the heating region is smaller than the width of the opening 100 such that on both lateral sides of the heating region an open portion of the opening 100 is formed. The open portions are not covered by mesh. The tin-plated mesh of the side portions of the filament arrangement forms a more plane contact area than the mesh itself. The contact areas are for contacting the heater assembly by an electrical connector from for example a battery.

In the example of FIG. 3 solid aerosol-forming substrate (not shown) is provided on the entire top surface of the heater assembly except for the opening 100 and filament assembly 11, that is, on the visible base surface 10 and on the metal sheets 16. For good contacting of the metal sheets 16 portions of the sheets may be kept without solid aerosol-forming substrate. However, due to the softness of the solid aerosol-forming substrate layer, contact element such as pogo pins may easily pass through an aerosol-forming substrate layer.

Figure 4:
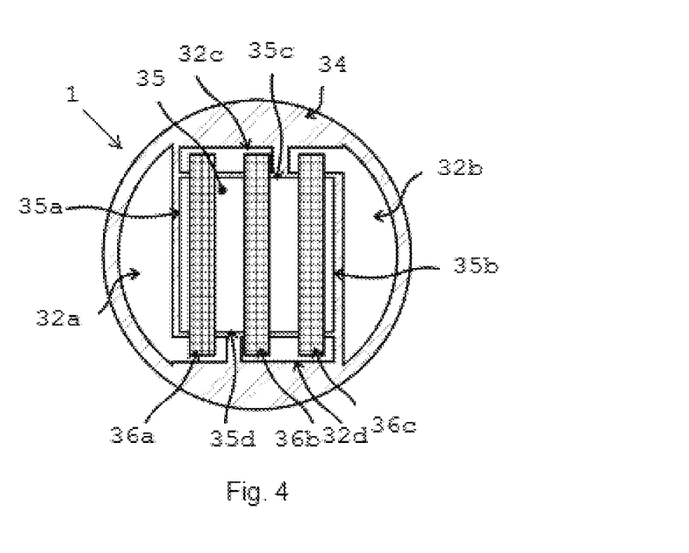
FIG. 4 is an illustration of a heater assembly with three heater elements according to at least one example embodiment.

In FIG. 4 another example embodiment of the heater assembly 1 is depicted, in which three substantially parallel heater elements 36a, 36b, 36c are electrically connected in series. The heater assembly 1 comprises an electrically insulating base 34 having a square aperture 35 formed in it. The size of the aperture 35 is about 5 mm×5 mm in this example, although it will be appreciated that other shapes and sizes of aperture could be used as appropriate for the particular application of the heater. A first and a second electrical contact 32a, 32b are provided at opposite sides of the aperture 35 and extend substantially parallel to the side edges 35a, 35b of the aperture 35. Two additional contacts 32c, 32d are provided adjacent parts of opposing side edges 35c, 35d of the aperture 35. The first heater element 36a is connected between the first contact portion 32a and the additional contact portion 32c. The second heater element 36b is connected between additional contact portion 32c and additional contact portion 32d. The third heater element 36c is connected between additional contact portion 32c and the second contact portion 32b. In this embodiment the heater assembly 1 comprises an odd number of heater elements 36, namely three heater elements and the first and second contact portions 32a, 32b are located on opposite sides of the aperture 35 of the base 34. Heater elements 36a and 36c are spaced from the side edges 35a, 35c of the aperture such that there is no direct physical contact between these heater elements 36a, 36c and the insulating base 34. Without wishing to be bound by any particular theory, it is thought that this arrangement can reduce heat transfer to the insulating substrate 34 and can allow for effective volatilization of the liquid aerosol-forming substrate.

In at least one example embodiment, small or large heat transfer from the heater elements 36a, 36b, 36c may heat the solid aerosol-forming substrate on the heater assembly 1. In at least one example embodiment, as shown in FIG. 4, the visible portions of the top surface of the base 34 are indicated by a line hatching and may be provided with solid aerosol-forming substrate. If the solid aerosol-forming substrate is applied after assembly of the heater assembly, the solid aerosol-forming substrate may be provided on the hatched base surface as well as on the contacts 32a, 32b, 32c, 32d, thus on all the heater surface except the aperture 35 and the three heater elements or at least except the three heater element portions extending over the aperture 35.

Figure 5:
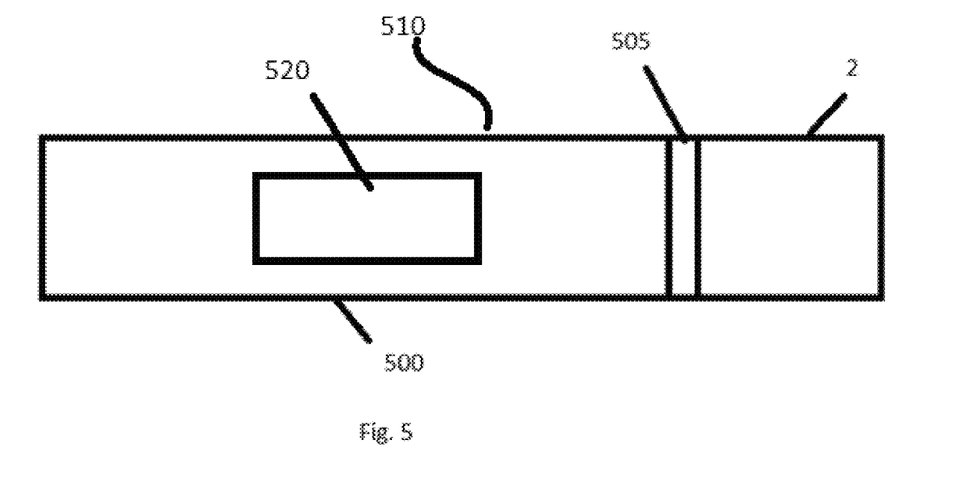
FIG. 5 is a schematic illustration of an aerosol-generating system including the cartridge of FIGS. 1 and 2 according to at least one example embodiment.

FIG. 5 is a schematic illustration of an aerosol-generating system including the cartridge of FIGS. 1 and 2 according to at least one example embodiment.

In at least one example embodiment, as shown in FIG. 5, an electrically operated aerosol-generating device 510 includes the cartridge 2 and a battery section 500. The battery section houses a power source 520. The cartridge 2 is connectable to the battery section 500 by a connector 505 that is configured to electrically connect the filament arrangement of the fluid permeable heater to the power source 520.

I claim:

1. A cartridge for an aerosol-generating device, the cartridge comprising:
    a cartridge body including,
        a reservoir in the cartridge body, the reservoir configured to store an aerosol-forming liquid,
        a heater assembly at one end of the cartridge body, the heater assembly configured to receive the aerosol-forming liquid from the reservoir, the heater assembly including,
        an electrically conductive filament arrangement; and
        a base defining an opening through the base, the base including,
            a solid aerosol-forming substrate on the base, the solid-aerosol-forming substrate in the form of an aerosol-forming sheet including at least one aerosol-former, and
            a thermally conductive material configured to conduct heat from the electrically conductive filament arrangement to the solid aerosol-forming substrate, the electrically conductive filament arrangement over the opening of the base, and
        electrical contacts configured to engage corresponding electrical contacts in an aerosol-generating device, the heater assembly configured to heat the aerosol-forming liquid received from the reservoir,
        wherein heater assembly and cartridge body are arranged such that the solid aerosol-forming substrate is on a top side of the heater assembly away from the cartridge body.

2. The cartridge according to claim 1, wherein the cartridge body defines an outlet opening, the outlet opening being aligned with the opening in the base of the heater assembly.

3. The cartridge according to claim 1, wherein the aerosol-forming liquid includes a nicotine-containing aerosol-forming liquid and the solid aerosol-forming substrate contains tobacco.

4. The cartridge according to claim 1, wherein the solid aerosol-forming substrate is a tobacco containing aerosol-forming substrate.

5. The cartridge according to claim 1, wherein the filament arrangement is a flat filament arrangement.

6. The cartridge according to claim 1, wherein the heater assembly is a flat fluid permeable heater assembly.

7. A cartridge for an aerosol-generating device, the cartridge comprising:

a cartridge body including,
   a reservoir in the cartridge body, the reservoir configured to store an aerosol-forming liquid,
   a heater assembly at one end of the cartridge body, the heater assembly configured to receive the aerosol-forming liquid from the reservoir, the heater assembly including,
   an electrically conductive filament arrangement; and
   a base defining an opening through the base, the base including,
     a solid aerosol-forming substrate on the base, the solid-aerosol-forming substrate in the form of an aerosol-forming sheet including at least one aerosol-former, and
     a thermally conductive material configured to conduct heat from the electrically conductive filament arrangement to the solid aerosol-forming substrate, the electrically conductive filament arrangement over the opening of the base, and
   electrical contacts configured to engage corresponding electrical contacts in an aerosol-generating device, the heater assembly configured to heat the aerosol-forming liquid received from the reservoir, wherein the opening of the base of the heater assembly is in a central portion of the cartridge and the solid aerosol-forming substrate is arranged circumferentially around the opening.

8. The cartridge according to claim 7, wherein the solid aerosol-forming substrate is a tobacco containing aerosol-forming substrate.

9. The cartridge according to claim 7, wherein the filament arrangement is a flat filament arrangement.

10. The cartridge according to claim 7, wherein the heater assembly is a flat fluid permeable heater assembly.

\* \* \* \* \*